(12) United States Patent
Koch et al.

(10) Patent No.: US 11,979,681 B2
(45) Date of Patent: May 7, 2024

(54) IMAGE RECORDING UNIT

(71) Applicant: AMBU A/S, Ballerup (DK)

(72) Inventors: Jakob Koch, Lyngby (DK); Brian Nielsen, Næstved (DK)

(73) Assignee: AMBU A/S, Ballerup (DK)

( * ) Notice: Subject to any disclaimer, the term of this patent is extended or adjusted under 35 U.S.C. 154(b) by 91 days.

(21) Appl. No.: 17/859,869

(22) Filed: Jul. 7, 2022

(65) Prior Publication Data

US 2023/0010235 A1  Jan. 12, 2023

(30) Foreign Application Priority Data

Jul. 8, 2021 (EP) ..................... 21184507

(51) Int. Cl.
| | |
|---|---|
| *H04N 7/18* | (2006.01) |
| *G06F 16/58* | (2019.01) |
| *H04L 9/08* | (2006.01) |
| *H04N 5/77* | (2006.01) |
| *H04N 5/913* | (2006.01) |

(52) U.S. Cl.
CPC ............... *H04N 5/77* (2013.01); *G06F 16/58* (2019.01); *H04L 9/088* (2013.01); *H04N 5/913* (2013.01); *H04N 7/183* (2013.01)

(58) Field of Classification Search
CPC .......... H04N 7/183; H04N 5/77; H04N 5/913; G06F 16/58; H04L 9/088
USPC .............................................. 348/689, 45, 65
See application file for complete search history.

(56) References Cited

U.S. PATENT DOCUMENTS

| | | | |
|---|---|---|---|
| 7,519,591 B2 | 4/2009 | Landi et al. |
| 8,166,313 B2 | 4/2012 | Fedtke |
| 8,589,183 B2 | 11/2013 | Awaraji et al. |
| 9,211,056 B2 | 12/2015 | Geisser et al. |
| 9,503,645 B2 | 11/2016 | Ju et al. |
| 9,795,277 B2 | 10/2017 | Fujita et al. |
| 9,841,280 B2 | 12/2017 | Amling et al. |
| 9,847,002 B2 | 12/2017 | Kiani et al. |
| 9,949,627 B2 | 4/2018 | Oskin et al. |
| 9,993,207 B2 | 6/2018 | Al-Ali et al. |
| 10,004,382 B2 | 6/2018 | Umemoto |

(Continued)

FOREIGN PATENT DOCUMENTS

| EP | 2923651 B1 | 4/2019 |
|---|---|---|
| WO | 2005109297 A2 | 11/2005 |

OTHER PUBLICATIONS

ESR in related European application No. 21184507.8, dated Nov. 8, 2021.

*Primary Examiner* — Sherrie Hsia
(74) *Attorney, Agent, or Firm* — Faegre Drinker Biddle & Reath LLP (57) ABSTRACT

A method implemented by an image recording unit having a normal state and an error state of operation. The method includes: receiving metadata specifying information about a patient and/or an endoscopic procedure; receiving images generated by an image sensor of an endoscope, the images corresponding to optical images received by the image sensor and comprising single images and/or a stream of images; controlling a display to show the images; in response to a first user input in the normal state, storing the images and the metadata in a memory of the image recording unit, and in the error state, overwriting with new data at least some of the metadata.

22 Claims, 6 Drawing Sheets

(56) References Cited

U.S. PATENT DOCUMENTS

| | | |
|---|---|---|
| 10,628,608 B2 | 4/2020 | Hebert et al. |
| 10,835,106 B1 | 11/2020 | Ubbesen et al. |
| 10,980,397 B1 | 4/2021 | Ubbesen et al. |
| 11,109,741 B1 | 9/2021 | Ubbesen et al. |
| 11,166,622 B2 | 11/2021 | Ubbesen et al. |
| 11,166,624 B2 | 11/2021 | Ubbesen et al. |
| 11,266,297 B2 | 3/2022 | Ubbesen et al. |
| 2009/0077024 A1 | 3/2009 | Abraham-Fuchs et al. |
| 2010/0036676 A1 | 2/2010 | Safdi et al. |
| 2012/0130160 A1 | 5/2012 | Borrye et al. |
| 2012/0162401 A1 | 6/2012 | Melder et al. |
| 2014/0156988 A1 | 6/2014 | Takahashi et al. |
| 2015/0033356 A1 | 1/2015 | Takenouchi |
| 2015/0320296 A1* | 11/2015 | Morita .................... G06T 7/246 348/65 |
| 2016/0014328 A1* | 1/2016 | Rokutanda ............... G06T 7/60 348/65 |
| 2016/0331213 A1 | 11/2016 | Kim |
| 2017/0020627 A1 | 1/2017 | Tesar et al. |
| 2017/0249432 A1 | 8/2017 | Grantcharov |
| 2018/0098684 A1 | 4/2018 | Hagihara et al. |
| 2019/0191963 A1 | 6/2019 | Kuhn et al. |
| 2019/0206562 A1 | 7/2019 | Shelton, IV et al. |
| 2020/0093506 A1 | 3/2020 | Leimbach et al. |
| 2021/0259517 A1 | 8/2021 | Ubbesen |

* cited by examiner

IMAGE RECORDING UNIT

CROSS REFERENCE TO RELATED APPLICATIONS

This application claims priority from and the benefit of European Patent Application No. EP21184507, filed Jul. 8, 2021; the contents of the aforementioned application are incorporated herein by reference in their entirety.

TECHNICAL FIELD

The present disclosure relates to image recording unit for recording images generated by a medical visualization device, such as an endoscope, a method of recording images, a computer program product, and a visualization system including the image recording unit. In particular, the disclosure relates to a method to anonymize the images in the image recording unit.

BACKGROUND

Endoscopes are widely used in hospitals for visually examining body cavities and obtaining samples of tissue identified as potentially pathological. An endoscope typically comprises an image sensor arranged at the distal end of the endoscope either looking forward or to the side. An endoscope is further typically provided with a working channel allowing a medical tool, such as a gripping device, a suction device, or a catheter, to be introduced therethrough.

An important part of the work for a medical professional is to document the result of an endoscopic procedure. As an example, a medical professional may need to document the discovery of a pathological condition. Additionally, a medical professional may need to document that a particular part of the body has been examined.

This is typically done by saving still images or videos from different parts of the examination using an image recording unit. An image recording unit may be incorporated into a display unit for displaying the images or provided as a standalone unit communicatively connectable to the display device. The images are typically stored with metadata describing information about the patient and/or the performed procedure. Images can be still images or a plurality of images in a video.

When an image recording unit malfunctions it may require a technician to investigate the problems and find a solution. This may be problematic as the technician may not be authorized to access patient's personal information that may be present in the metadata. To prevent that the technician accesses the personal information, particularly if the image recording unit is shipped out for repairs, the image recording unit can be reset. Resetting the image recording unit can delete all data stored thereon.

However, by resetting the image recording unit, the state of the image recording unit is significantly changed, whereby the nature of the malfunction may also be significantly changed or even disappear, thereby preventing the technician from discovering the true source of the error.

Thus, it remains a problem to provide a medical visualization device that is easier to service.

SUMMARY

According to a first aspect, the present disclosure relates to an image recording unit for recording endoscope images captured by an image capturing device of an endoscope, the image recording unit comprising a processing unit, one or more memory units operationally connected to the processing unit, a connection unit, the processing unit is operationally connectable to the image capturing device and a display for displaying images captured by the image capturing device, the processing unit being operationally connectable to the image capturing device via the connection unit and has a normal operational state and an error state, wherein the processing unit is configured to, when being in the normal operational state, in connection with an endoscopic procedure on a patient: receive metadata specifying information about the patient and/or information about the endoscopic procedure; continuously receive images captured by the image capturing device of the endoscope and control the display to show the received images; store permanently in the one or more memory units in response to a user input one or more single images or one or more streams of images received from the image capturing device together with the received metadata, whereby a database is created in the one or more memory units storing for a plurality of previously performed endoscopic procedures one or more single images or stream of images together with the metadata, wherein the processing unit is configured to, when being set in the error state, overwrite with new data at least some of the metadata for the plurality of previously performed endoscopic procedures with new data.

Consequently, by overwriting at least some of the metadata with new data the state of the image recording unit may be kept at least closer to the state it had when a malfunction occurred. This may enable a technician more easily to determine the root cause of the problem.

The processing unit of the image processing device may be any processing unit, such as a central processing unit (CPU), a graphics processing unit (GPU), a microcontroller unit (MCU), a field-programmable gate array (FPGA), or any combination thereof. The processing unit may comprise one or more physical processors and/or may be combined by a plurality of individual processing units. The new data may be generated by the processing unit of the image recording unit, stored on the one or memory units, or provided to the image recording unit from another unit.

The connection unit may be a physical connection port. Alternatively, the connection unit may be wireless connection unit configured to communicate wireless directly with the endoscope or a wireless adapter connected to the endoscope.

In some embodiment the new data does not encode the metadata, i.e. the new data is generated from a process that does not rely on the metadata as input.

Consequently, it may be secured that the overwritten metadata may not be made available to unauthorized personal that successfully has decoded the new data. As an example, if the new data was generated by an encryption algorithm encrypting the metadata using an encryption key, unauthorized personnel could get access to the metadata by breaking the encryption e.g. by guessing the encryption key or using a brute force approach.

The new data may have a size substantially corresponding to the size of the overwritten metadata. The new data may also have a form corresponding to the overwritten metadata e.g. if the overwritten metadata specifies patient names then the new data may specify made up patient names, if the overwritten metadata specifies patient ages then the new data may specify made up patient ages etc.

In some embodiments the processing unit is switchable from the normal operational state to the error state in response to a first user input.

Consequently, a user may in an easy way secure the metadata before providing the image recording unit to a service department.

In some embodiments the image recording unit further comprises a user input unit operationally connected to the processing unit, and wherein the first user input can be generated using the user input unit.

The input unit may be a touch screen or a physical button. The physical button may be provided in a depression having a size preventing a user from accessing the button using a finger, whereby a user may be forced to use a tool to press the button e.g. sharp object such as the distal end of a ball pen or an unfolded paper clip. This may prevent the user from accidental setting the image recording unit in the error state.

In some embodiments, the image recording unit comprises a communication unit for receiving messages from another processing unit, wherein the first user input can be received via the communication unit.

Consequently, a technician may remotely prepare the image recording unit for maintenance.

In some embodiments the image recording unit comprises an input unit, and wherein the processing unit in response to having received the first user input in a message from another processing unit is configured to control the display to display a message prompting the user to confirm switching the state of the processing unit from the normal operational state to the error state via the input unit.

Consequently, it may be prevented that a wrong image recording unit is set into the error state potentially overwriting important data and interrupting a medical procedure.

In some embodiments, the processing unit is configured to when being in the error state prevent images captured by the image capturing device to be shown on the display.

Consequently, it may be prevented that a damaged image recording unit is used for medical procedures.

In some embodiments, the processing unit is configured to create a safety copy of the overwritten metadata before it is overwritten.

Consequently, the safety copy may be used to re-create the overwritten metadata when the image recording unit is returned.

In some embodiments the processing unit is configured to encrypt the safety copy using an encryption key.

In some embodiments the processing unit is configured to store the encrypted safety copy on a memory unit remote from the image recording unit, and wherein the encryption key is stored on the one or more memory units of the image recording unit.

Consequently, it may be secured that the overwritten data can only be accessed by a party having access to both the image recording unit and the encrypted safety copy.

In some embodiments the one or more single images or one or more streams of images stored in the database comprises an information zone, wherein the processing unit is configured to insert a part of the metadata into the information zone, and wherein the processing unit is configured to, when being set in the error state, re-process the one or more single images or one or more streams of images stored in the database to remove at least some of the metadata stored in the information zone.

Consequently, even metadata inserted into stored images may be overwritten, while enabling the remaining parts of the images to be left unaltered. Thus, valuable information in the stored images for identifying a potential malfunction may be kept accessible to a technician.

According to a second aspect, the present disclosure relates to an endoscopic system comprising an image recording unit as disclosed in relation to the first aspect and an endoscope comprising an image capturing device.

According to a third aspect, the present disclosure relates to a method of recording images captured by an image capturing device of an endoscope, the method comprising: receiving metadata specifying information about a patient and/or information about an endoscopic procedure; continuously receiving images captured by the image capturing device of an endoscope and control a display to show the received images; storing permanently in one or more memory units in response to a user input one or more single images or one or more streams of images received from the image capturing device together with the received metadata, wherein a database is created in the one or more memory units storing for a plurality of previously performed endoscopic procedures one or more single images or stream of images together with the metadata, wherein the method further comprises the step of at least partly anonymizing the database by overwriting at least some of the metadata for each of the plurality of previously performed endoscopic procedures with new data.

According to a fourth aspect, the present disclosure relates to a computer program product comprising program code means adapted to cause a processing unit to perform the steps of the method disclosed in relation to the third aspect, when said program code means are executed by the processing unit.

In some embodiments said computer program product comprises a non-transitory computer-readable medium having stored thereon the program code means.

The different aspects of the present disclosure can be implemented in different ways including display units, endoscopic systems, a methods of recording images and computer program product described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present disclosure, will be further elucidated by the following illustrative and non-limiting detailed description of embodiments of the present disclosure, with reference to the appended drawings, wherein.

DETAILED DESCRIPTION

In the following description, reference is made to the accompanying figures, which show by way of illustration how the embodiments of the present disclosure may be made and practiced.

Figure 1:
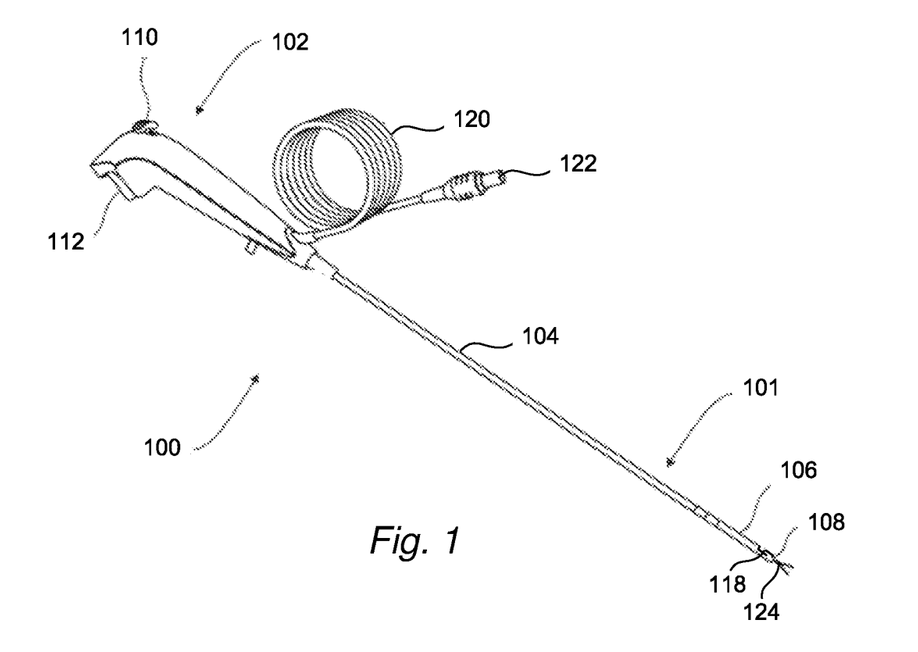
FIG. 1 shows an example of an endoscope.
Figure 2:
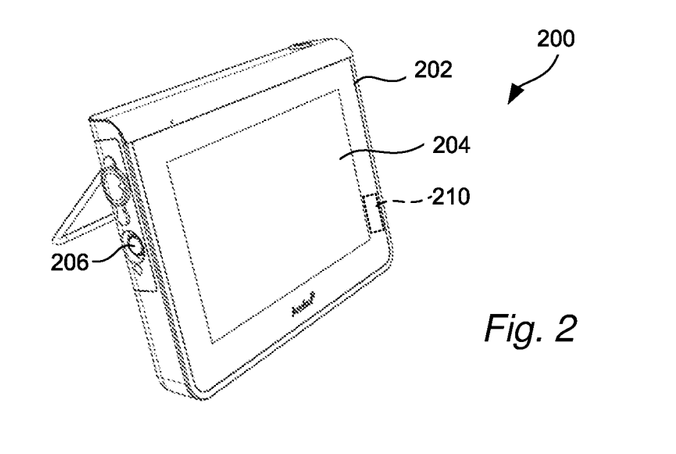
FIG. 2 shows an embodiment of a image recording unit that can be connected to the endoscope shown in FIG. 1.

FIG. 1 illustrates an example of an endoscope 100. FIG. 2 illustrates an example of an image recording unit 200. Together, the endoscope 100 and the image recording unit 200 may be referred to as a visualization system 10. This endoscope may be adapted for single-use, by including parts that are not sterilizable, to reduce its cost. The endoscope 100 is provided with a handle 102 attached to an insertion cord 101 including an insertion tube 104, a bending section 106 and a tip part 108. The tip part 108 includes an image sensor 118. A cable 120 with a cable connector 122 is also shown. The cable connector 122 can be plugged into a connection unit 206 of an image recording unit 200 (see FIG. 2) to establish communications between the image sensor 118 and the image recording unit 200. The endoscope 100, having an image sensor and being designed to inspect and/or treat internal tissue of a patient, is an example of a medical visualization device. Medical visualization devices include endoscopes, laryngoscopes, laparoscopes, endotracheal tubes, catheters, and any other medical device comprising an image sensor and designed to inspect and/or treat internal tissue of a patient.

The insertion cord 101 may be provided with one or several working channels such that medical instruments 124, e.g. a gripping device, a catheter, a portion of laser, etc., may extend from the tip part 108 to inspect and/treat internal tissue of a patient. One or several exit holes of the one or several channels may be provided in the tip part 108. The bending section 106 can be bent in different directions with respect to the handle 102. The bending section 106 may be controlled by the operator by using a knob 110 placed on the handle 102. The knob 110 is actuated by a thumb of the operator to pull/push steering cables connected to the distal tip part 108 and thereby control the orientation of the image sensor 118. Other steering designs are also possible. A push button 112 may be used to actuate a vacuum valve and thus provide suction via the working channel.

The tip part 108 includes the image sensor 118, which may be a CMOS sensor or any other image capturing device, and one or several light emitting devices, such as light emitting diodes (LEDs), fibers, or any other light emitting devices. As is known in the art, the image sensor 118 includes pixels that convert light representative of optical images into electrical signals. The image sensor 118 can adjust how it generates the electrical signals, for example by adjusting white balance, exposure, and other parameters, to produce images corresponding to the optical images optimized by, for example, avoidance of overexposed or underexposed pixels. Thus, herein the term "optical image" refers to the light captured by the image sensor and "output image" refers to the output of the image sensor. The image sensor may transmit the images it generates in rapid succession, referred to as "video" or "video stream", via an image bus comprised by a serial or parallel communication channel. The image generated by the image sensor may be referred to as "image," "image data," or "image file," which terms are also used to refer to adaptations of the image made by the image recording unit to, for example, adapt the image to the display format, create low resolution copies for a database or to present with the display along full resolution versions, etc.

FIG. 2 illustrates an embodiment of the image recording unit 200 configured to display the images so that an operator is able to see and analyze an inside of the human body to, for instance, localize a position for taking a sample. In addition, the operator will be able to control the medical instrument in a precise manner due to the provided visual feedback. Further, since some diseases or health issues may result in a shift in natural colors or other visual symptoms, the operator is provided with valuable input for making a diagnosis based on the images. The image recording unit 200 comprises a housing 202, a display 204, a connection unit 206, and a processing unit 210 (only schematically shown). As shown, the connection unit 206 is configured to receive the cable connector 122 of the endoscope 100 and thereby operationally connect the endoscope 100 to the processing unit 210. The connection unit 206 may be a physical connection port further configured to provide power to the endoscope 100. The connection unit 206 may, instead, comprise a wireless transceiver operable to communicate wirelessly with a wireless transceiver located in the endoscope, in which case a battery is located in the handle 102 to power the image sensor and the transceiver. The connection units, regardless of implementation, are configured to transmit configuration data to the endoscope and to transmit the output images to the processing unit 210.

Figure 3:
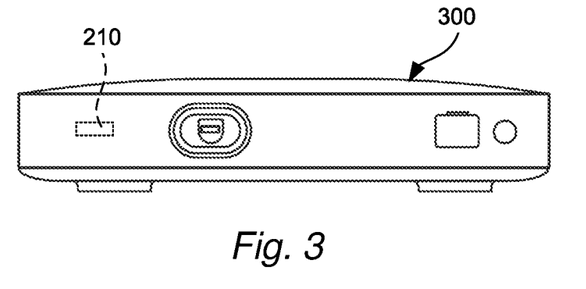
FIGS. 3 and 4 show front plan and rear perspective views of another embodiment of an image recording unit that can be connected to the endoscope shown in FIG. 1.
Figure 4:
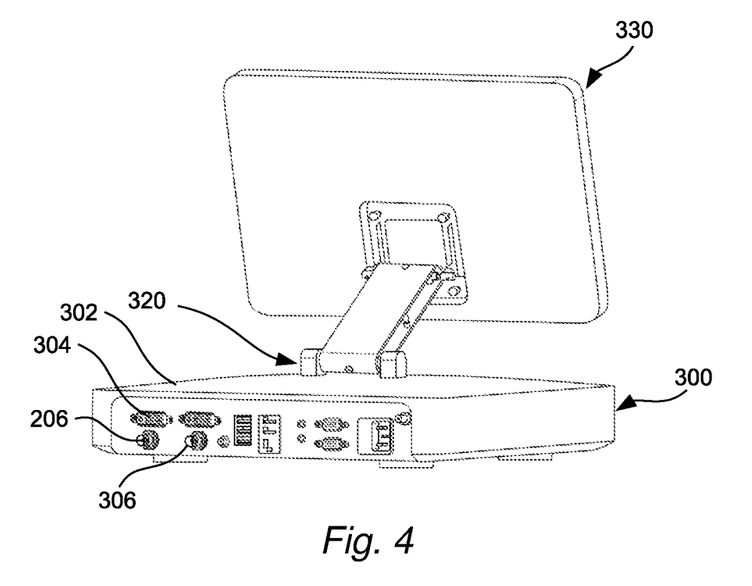

FIGS. 3 and 4 are front elevation and rear perspective views of another embodiment of an image recording unit, denoted by numeral 300. Unlike the image recording unit 200, the image recording unit 300 does not include a display 204. Instead, a display support bracket 320 can be removably attached to a housing 302 to support therewith a display device 330 including the display 204. The display support bracket 320 can be removed and the image recording unit 300 can thus be positioned in a discrete location where it does not interfere with the medical procedure. The image recording unit 300 includes an output port 304 configured to communicativelly couple a display device not necessarily mounted on the housing 302.

Figure 5:
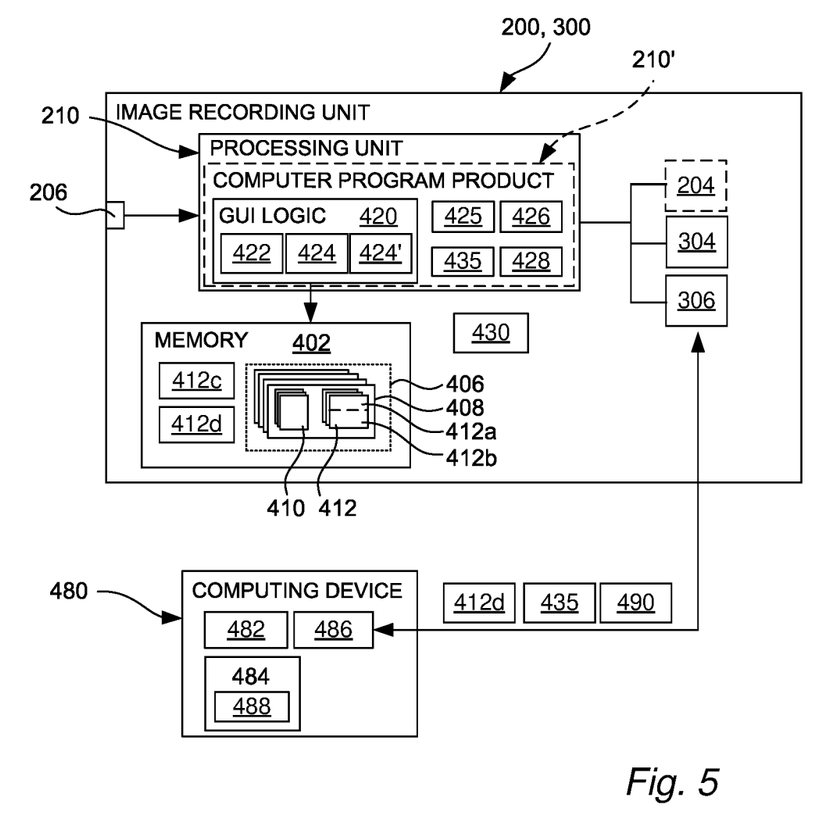
FIG. 5 shows a block diagram of an embodiment of an image recording unit according to the disclosure.

FIG. 5 is a schematic drawing of an embodiment of the image recording unit 200. The image recording unit 200, 300 comprises the processing unit 210, one or more memory units 402 operationally connected to the processing unit 210, the output port 304, and the connection unit 206. The display 204 is shown in dashed lines to indicate that it is an optional component. The logic components of the image recording unit 200 may be embedded in a computer program product 210'. The computer program product 210' may comprise program code in the form of a disk, FPGA, disk image, or files configured to transfer the logic into a disk.

The image recording unit 200, 300 may include a connection unit 306 configured to communicativelly couple the image recording unit 200, 300 with a computing device 480. The connection unit 306 can be configured to receive a cable connector of a cable connecting the connection unit 306 with a connection unit 486 of the computing device 480. Alternatively, the connection units 306, 486 may, instead, comprise wireless transceivers operable to communicate wirelessly with each other. The connection unit 306 may comprise a WiFi access point to establish a WiFi wireless network accessible by the computing device 480. The connection units 306, 486 may also comprise Bluetooth or other wireless transceivers known in the art. The cable may be a network cable.

The computing device 480 is any device that includes a processing unit 482 and a memory 484 comprising processing instructions operable to allow communications with the image recording unit 200, 300. The computing device 480 comprises a user interface with which the user can control the computing device 480. Example user interfaces include displays, keyboards microphones, touch-screens and any other user interface known in the art. The user interface may be a GUI 488. Example computing devices include workstations, portable computers, tablets, mobile phones, and the like. The processing unit 482 and the memory 484 can be integrated in a single integrated circuit.

The processing unit of the image processing device may be a CPU, a GPU, an MCU, a FPGA, or any combination thereof. The processing unit may comprise one or more physical devices.

According to a preferred embodiment, logic comprising processing instructions operable to perform the methods described herein is comprised in the FPGA. The processing unit 210 may also comprise a CPU configured to handle the peripheral functions. Advantageously, the FPGA may be easily updated and programmed with the logic. The FPGA is capable of rapid power-up (i.e. short boot-up time) and thus is useful in emergency situations. FPGAs process data very fast compared to other memory/instruction combinations and are re-programmable. Therefore FPGAs facilitate presentation of images captured by the medical visualization device in real-time ("live images," "live video" or "live views") with minimal latency so that the physician observing the live view can take immediate actions even in emergency situations. As technology evolves, the functionality of the FPGA may be combined with a fast processor. The image recording unit 200, 300 is therefore not limited to the precise packaged integrated circuits described with reference to FIG. 5 but can be constructed to take advantage of design and cost targets and future video processing technologies. For example, faster/more costly memory may be used to increase graphics processing speed. Graphics processing may be provided in the FPGA or a processor that incorporates graphics processing logic may be used instead.

The term "logic" as used herein includes software and/or firmware executing on the processing unit, which may comprise, as stated, one or more processing devices, application-specific integrated circuits, field-programmable gate arrays, digital signal processors, hardwired logic, or combinations thereof. Therefore, various logic may be implemented in any appropriate fashion and would remain in accordance with the embodiments herein disclosed.

The processing unit 210 may comprise graphical user interface (GUI) logic 420 operable to generate a GUI 422 presented with display 204 and/or an external display. The GUI can be responsive to user inputs received via a user interface, for example the display 204, when it is a touch-screen, or other user interfaces having user input capabilities. The processing unit 210 or the memory 402 may comprise, embedded therein, an encryption key 426, e.g. a private encription key, and encryption logic 428, which are known in the art.

The GUI may present various icons corresponding to actions selectable by the user with any of the above-described user input devices, to for example store or record a copy of a live image, store or record a portion of video corresponding to live images, invert the views, apply correction curves to the image data to reduce overexposure, etc. The icons and the GUI logic perform the user indicated command and are one example of a user input unit (working together with the input sensors and the outputs of the touch-screen), which may be referred to as a "button" and denoted by numerals 424, 424'. The button 424, 424' can be used at different times to receive from the user, and in response generate, the first user input 425 and the second user input 435, which are signals associated with the action taken by the user with the button 424, 424'.

Figure 5A:
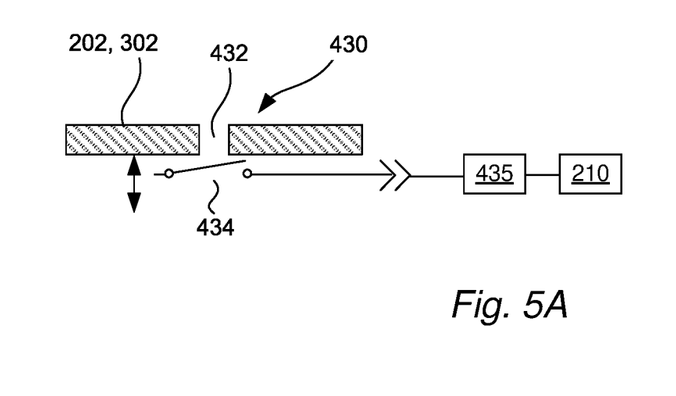
FIG. 5A shows a schematic diagram of a recessed user input switch.

Another example is a physical user input unit, designated as button 430 in FIG. 5A, comprising an aperture 432 in the housing 202, 302 and a switch 434, e.g. an electric switch communicatively connected to the processing unit 210. Activation of the switch with a pin sends a second user input 435 to the processing unit 210 to switch the operating state to the error state.

The communication unit 306 may be configured to receive a message 490 and the second user input 435 from the processing unit 482, the processing unit 482 being separate from the image recording unit 200, 300, wherein the message 490 prompts a user to confirm, via the user input unit, switching of the processing unit 210 from the normal state to the error state. In response to receiving the second user input 435 from the processing unit 482, the processing unit 210 controls the display to show the message 490. The user may then confirm the intent to switch to the error state with any user input unit programmed for that purpose. Confirmation might not be required if using the button 430, which incorporates protection from inadvertent actuation.

The memory 402 may comprise a database 406 operable to manage a plurality of image files 408. Metadata is data about data and may be stored in the image files along with the images or in separate files. In some embodiments, the image files 408 comprise images (e.g. image rasters) 410 and metadata 412. Generally, metadata can comprise technical and content metadata. Technical metadata describes an image in a technical sense, such as its height and width, in pixels, or the type of compression used to store it, and is generally generated by the image sensor. Content metadata is mostly added by the user or the visualization system and may include keywords related to the image, captions, comments, time and date, and codes or descriptions indicative of a patient or procedure, among many other possibilities. The metadata may specify information about the patient and/or the endoscopic procedure associated with the images.

Storing metadata together with image data in the same image file provides encapsulation. With encapsulation, both types of data can be shared and exchanged reliably as one unit. Metadata that is stored in the image file format is referred to as embedded metadata. However, metadata can also be contained in a separate file that is associated with the image file.

A database can be provided to perform various functions. For example, the database can associate an image file with a file containing related metadata. The database can also be used to index saved image files for easy retrieval and review. Thus, the term "database" is used herein to refer to any mechanism that enables the association of files and, optionally, the addition of descriptive information in connection with a file. In one example, metadata associated with an image file is stored in the database instead of the image file.

The metadata may comprise general metadata 412*a* and private metadata 412*b*. The general metadata 412*a* is metadata that does not need to be safeguaded. Private metadata 412*b* is metadata that is to be safeguaded for any reason. Private metadata may include patient data, procedure data, or any other data of a sensitive nature. Of course, all the metadata 412 could be safeguarded, as described below, but safeguarding, for example, technical metadata adds computational cost without, in most cases, being necessary. Technical metadata may be used by the processing unit 210 to send configuration parameters to the image sensor to adjust future images as the images are generated and received.

The memory 402 may comprise dummy, or new, metadata 412c. The dummy metadata 412c may be used to replace private metadata 412b. The dummy metadata 412c may be selected to appear to contain private metadata, for example containing dummy patient names, dates etc. Alternatively, the dummy metadata 412c could be randomly generated or could contain information obtained from a file, which while not random would serve the purpose of overwriting private metadata 412b, as described below. The private metadata 412b is run through the encryption logic 428 to generate encrypted metadata 412d.

Having described the components of various embodiments of image recording units and visualization systems, attention is now directed to embodiments of methods to safeguard information.

Figure 6:
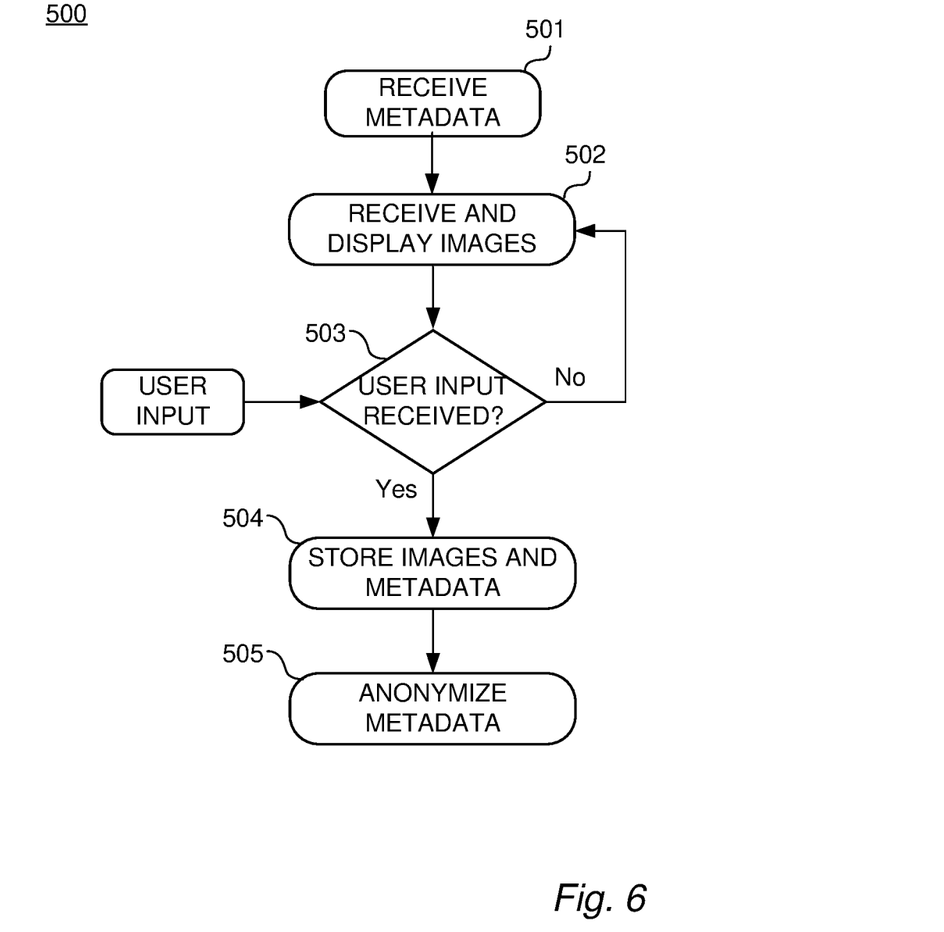
FIG. 6 shows a flowchart of an embodiment of a method of recording images captured by an image sensor of the endoscope shown in FIG. 1.

Referring to FIG. 6, a flowchart 500 of a method of recording images captured by an image sensor of a medical visualization device is shown. The method may be performed by the image recording unit 200, 300.

The method starts at 501, where in connection with an endoscopic procedure on a patient, metadata specifying information about a patient and/or information about an endoscopic procedure is received. By endoscopy procedure it is meant a procedure using a medical visualization device, such as an endoscope. The metadata may be received via any user interface, whether the user interface is provided by the image recording unit or a remote computing device communicatively connected with it. The metadata may also be embedded in a portable memory device, such as a USB key. The USB key may contain information from or about the physician or details about the procedure or the patient, which the physician may have saved for this purpose prior to the procedure. The safety copy, encrypted or not, of the anonymized metadata may also be stored in the USB key, which may include its own encryption to safeguard the information.

Next, at 502, also in connection with the endoscopic procedure, images captured by the image sensor are continuously received and a display is controlled to show the received images. By continuously received it is meant that the images are live images, captured and transmitted during the procedure by the image sensor at a predetermined frame rate. The processing unit 210 outputs video signals incorporating the GUI and the images. The video signals may be received by a memory buffer and the buffer may be read by the display or video output port to present the GUI and images. Techniques for presenting images are well known, including techniques using buffers or mapped memory Then, at 503, in response to a user input, one or more single images or one or more streams of images received from the image sensor, together with the received metadata, are stored in one or more memory units, at 504. The user input may be referred to as a "record" command. The record command can be, for example, an image record command or a video record command, which may comprise a start recording command and a stop recording command. Each of these options may comprise an icon or image presented with the display and associated with the respective action. When the user touches the display portion where the icon is located, the display receives the command, e.g. user input, from the user.

This results in that a database is created in the one or more memory units storing, for a plurality of previously performed endoscopic procedures, one or more single images or stream of images together with the metadata. The images and metadata associated with each image can be saved in a common image file 408 or in separate files or database fields.

Finally, at 505, the method comprises at least partly anonymizing the database or the metadata of the stored images. Anonymizing comprises removing identifying particulars or details from data. In some embodiments, anonymizing comprises overwriting at least some of the metadata for each of the plurality of previously performed endoscopic procedures with new, or dummy, data, as described with reference to FIG. 8. The new data may be generated by the processing unit of the image recording unit, stored on the one or memory units, or provided to the image recording unit from another image recording unit.

In some embodiments, anonymizing comprises implementing an alteration strategy such as character shuffling, character substitution, generalization, and the like. Anonymizing may comprise overwriting the private metadata 412b with the dummy metadata 412c.

In some embodiments, the image recording unit 200, 300 has a normal state of operation and an error state of operation. The user may cause the image recording unit 200, 300 to switch from the normal to the error state by activating a second user input, e.g. an "anonymize" command, via a user interface. Switching states may comprise setting a flag or bit or other memory device which the logic checks before performing certain actions. For example, the image recording unit 200, 300 may stop presenting images with the display if the unit is in the error state. The unit might also display a message indicating the current error state.

In some embodiments the unit might enter the error state due to an error. For example, the image recording unit 200, 300 may be programmed to recognize that certain errors are not recoverable and render the unit inoperable, such as certain hardware failures. Since the unit is inoperable it might enter the error state to preserve the private information. The anonymized images may also be saved to another computing device.

The user interface, or input unit, may be a touch-screen or a physical button. The physical button 430 may be provided below a surface having a small hole such that a user cannot actuate the user input with a finger and, instead, the user has to use a tool to press the physical button e.g. a pin, the distal end of a ball pen, an unfolded paper clip, etc. The surface may be a surface of the housing of the image recording unit 200, 300 and the small hole may have a diameter of 3 mm or less, for example. This may prevent the user from accidentally setting the image recording unit in the error state. Consequently, the user may in an easy way secure the metadata before providing the image recording unit to a service department.

Figure 7:
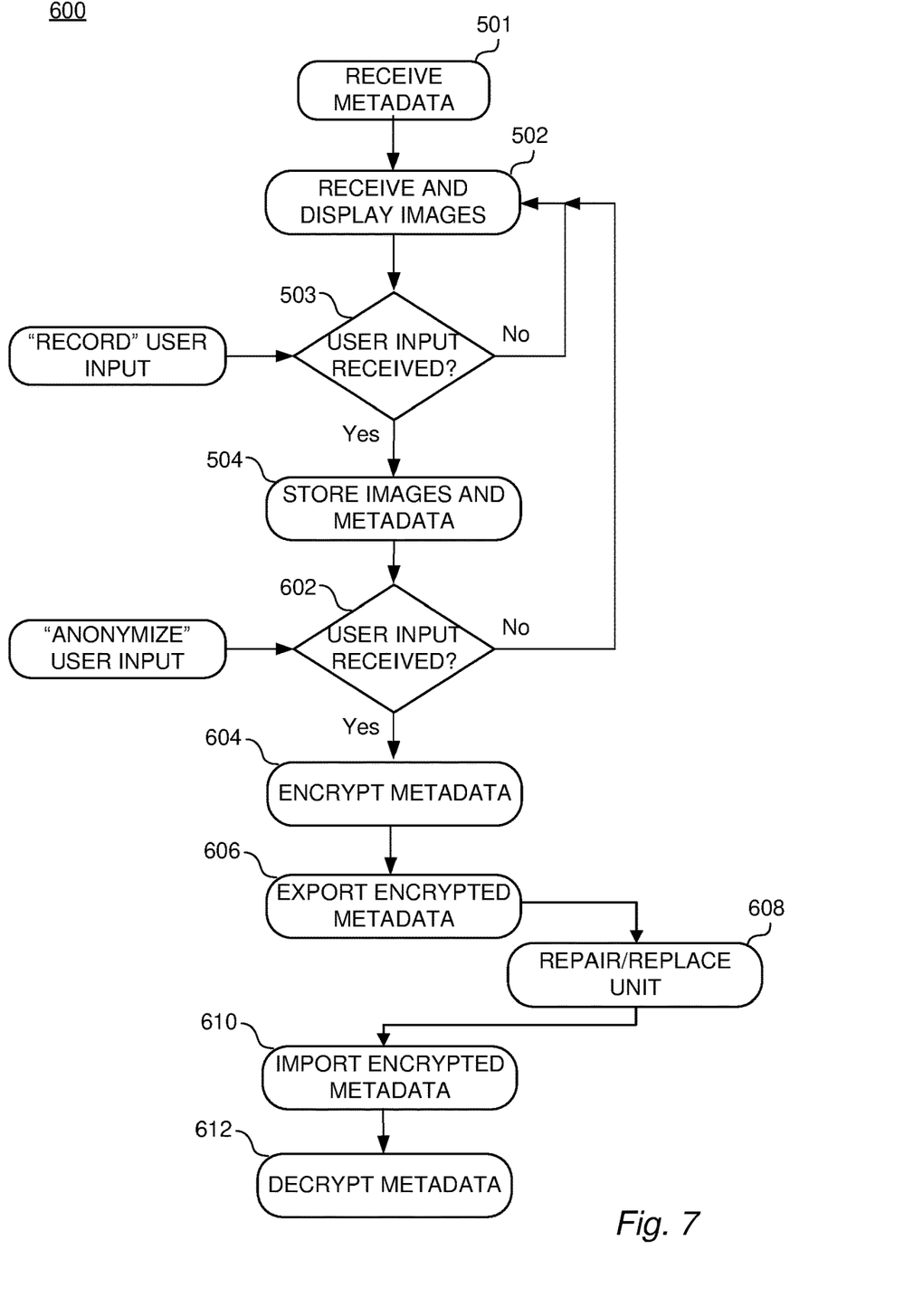
FIG. 7 shows a flowchart of an embodiment of a method of anonymizing image metadata.

A variation of the method described with reference to FIG. 6 will now be described with reference to FIG. 7, in which a flowchart 600 is shown. As in the flowchart 500, the method begins, from 501 to 504, with the reception of metadata and images, and the storing of the metadata and images responsive to a first user input, such as a "record" command.

Then, at 602, the image recording unit 200, 300 receives a second, or anonymize, user input. Until then the image recording unit 200, 300 continues receiving and showing images, and saving the images if the first user input was received.

Upon receipt of the second user input, and optionally of a confirmation user input, the image recording unit 200, 300 encrypts metadata, at 604. The encryption can be of all the image metadata or just the information designated as "private." The designation can be arbitrary but is intended to safeguard information identifying the patient. The private metadata may be read from the image files and encrypted, e.g. in the encrypted metadata file 412*d*, without first creating a safety copy. After encryption the private metadata in the unencrypted file in the image recording unit may be anonymized.

The encrypted metadata 412*d* is then exported, at 606, to a remote computing device or memory, e.g. USB key, so that the image recording unit 200, 300 can be sent for repair or be replaced, at 608.

Once the replaced or repaired image recording unit 200, 300 becomes available, the encrypted metadata is decrypted, at 612, and written to the image files or database to restore the image recording unit 200, 300 (or format the new unit) to the normal state in the condition it was prior to entering the error state. The error flag can then be toggled to the normal state.

Figure 8A:
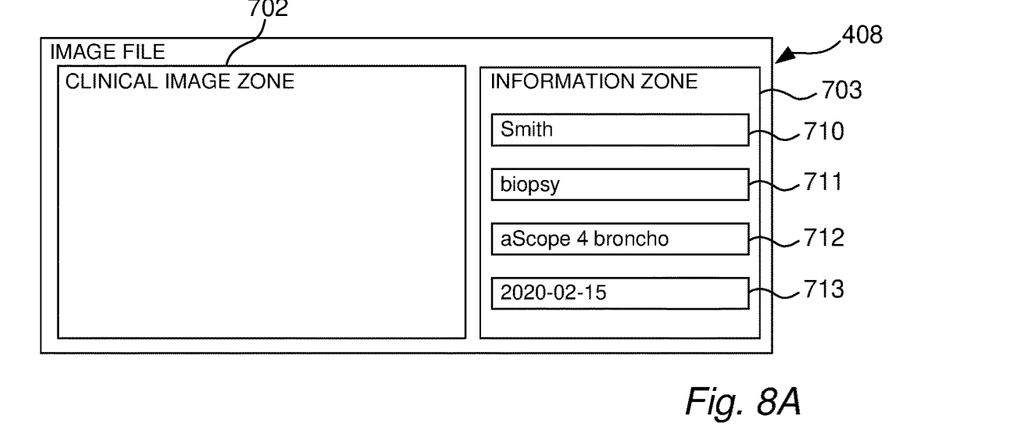
FIGS. 8A-C illustrate a method of re-processing images according to an embodiment of the disclosure.
Figure 8B:
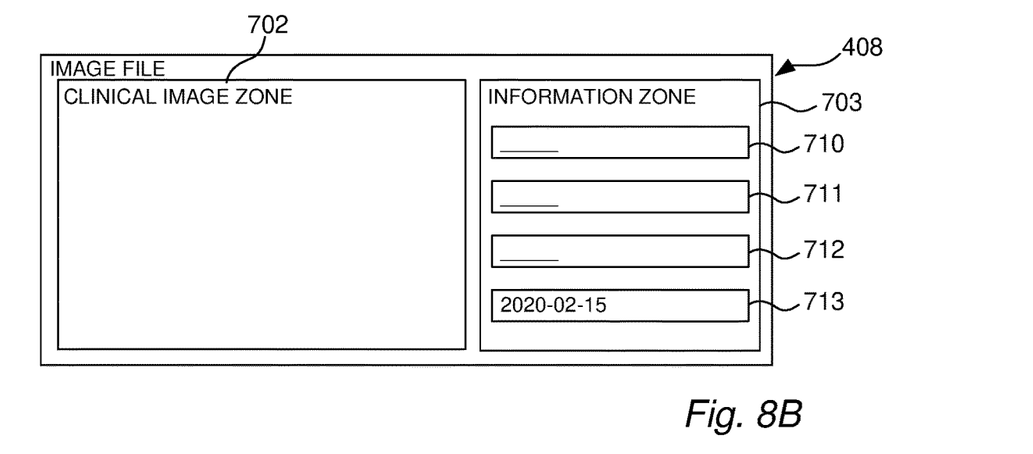
Figure 8C:
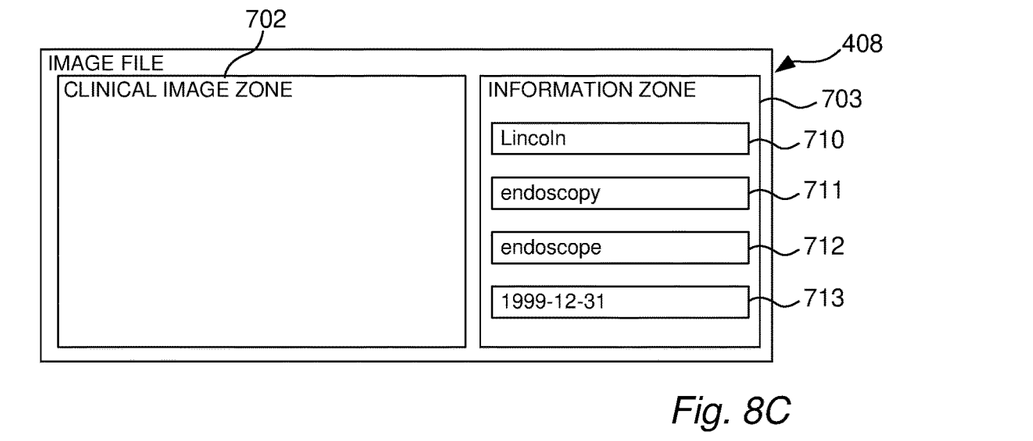

The foregoing embodiments depicted in FIGS. 6 and 7 will now be described with reference to FIGS. 8A-8C, depicting images and metadata. It should be understood that the depictions using zones are merely to illustrate one type of anonymization. In practice the image zones correspond to addresses to which data is written. FIG. 8A shows schematically an image file 408 stored in the database of an image recording unit according to an embodiment of the present disclosure. The image file 408 comprises clinical image zone 702 and an information zone 703. The clinical image zone 702 comprises the image 410 captured by an image sensor in connection with an endoscopic procedure on a patient. The image recording unit has received metadata specifying information about the patient and/or information about the endoscopic procedure. At least part of the metadata 412 is inserted into the information zone 703. The information zone 703 may comprise a first field 510 specifying the name of the patient, a second field 511 specifying the endoscopic procedure, a third field 512 specifying the type of endoscope used, and a fourth field 513 specifying the time of the endoscopic procedure. As shown, the fields include the following metadata: Smith, biopsy, aScopte 4 bronco and 2020-02-15.

FIG. 8B shows how the image file 408 may look after a processing unit of the image recording unit has been set in an error state and in response thereto has re-processed the image file 408 to remove at least some of the metadata stored in the information zone 703. In this example the information zone 703 has been replaced with dummy metadata 412*c* in fields 710-712, e.g. spaces.

By enabling a technician to review recorded endoscope images, the technician may be able to discover if the malfunction is a malfunction of the image recording unit or a malfunction an endoscope connected to the endoscope recording unit. Leaving the date in the images may assist the technician by, perhaps, correlating the date with image degradation or other timing events. Of course the dates can also be blanked.

FIG. 8C shows how the image file 408 may look after a processing unit of the image recording unit has been set in an error state and in response thereto has re-processed the image file 408 to remove at least some of the metadata stored in the information zone 703. In this example, the fields were rewritten with the following dummy metadata: Lincoln, endoscopy, endoscope, 1999-12-31.

The following items are examples and variations of various embodiments disclosed above:

1. An image recording unit for recording endoscope images captured by an image capturing device of an endoscope, the image recording unit comprising a processing unit, one or more memory units operationally connected to the processing unit, a connection unit, the processing unit is operationally connectable to the image capturing device and a display for displaying images captured by the image capturing device, the processing unit being operationally connectable to the image capturing device via the connection unit and has a normal operational state and an error state, wherein the processing unit is configured to, when being in the normal operational state, in connection with an endoscopic procedure on a patient: receive metadata specifying information about the patient and/or information about the endoscopic procedure; continuously receive images captured by the image capturing device of the endoscope and control the display to show the received images; store permanently in the one or more memory units in response to a user input one or more single images or one or more streams of images received from the image capturing device together with the received metadata, whereby a database is created in the one or more memory units storing for a plurality of previously performed endoscopic procedures one or more single images or stream of images together with the metadata, wherein the processing unit is configured to when being set in the error state overwrite at least some of the metadata for the plurality of previously performed endoscopic procedures with new data.

2. An image recording unit according to item 1, wherein the processing unit is switchable from the normal operational state to the error state in response to a first user input.

3. An image recording unit according to item 2, wherein the image recording unit further comprises a user input unit operationally connected to the processing unit, and wherein the first user input can be generated using the input unit.

4. An image recording unit according to item 2 or 3, wherein the image recording unit comprises a communication unit for receiving messages from another processing unit, wherein the first user input can be received via the communication unit.

5. An image recording unit according to item 4, wherein the image recording unit comprises an input unit, and wherein the processing unit in response to having received the first user input in a message from another processing unit is configured to control the display to display a message prompting the user to confirm switching the state of the processing unit from the normal operational state to the error state via the input unit.

6. An image recording unit according to any one of items 1 to 5, wherein the processing unit is configured to when being in the error state prevent images captured by the image capturing device to be shown on the display.

7. An image recording unit according to any one of items 1 to 6, wherein the processing unit is configured to create a safety copy of the overwritten metadata before it is overwritten.

8. An image recording unit according to item 7, wherein the processing unit is configured to encrypt the safety copy using an encryption key.

9. An image recording unit according to item 8, wherein the processing unit is configured to store the encrypted safety copy on a memory unit remote from the image recording unit, and wherein the encryption key is stored on the one or more memory units of the image recording unit.

10. An image recording unit according to any one of items 1 to 9, wherein the one or more single images or one or more streams of images stored in the database comprises an information zone, wherein the processing unit is configure to insert a part of the metadata into the information zone, and wherein the processing unit is configured to when being set in the error state re-process the one or more single images or one or more streams of images stored in the database to remove at least some of the metadata stored in the information zone.

11. An endoscopic system comprising an image recording unit according to any one of items 1 to 10 and an endoscope comprising an image capturing device.

12. A method of recording images captured by an image capturing device of an endoscope, the method comprises, in connection with an endoscopic procedure on a patient: receive metadata specifying information about a patient and/or information about an endoscopic procedure; continuously receive images captured by the image capturing device of an endoscope and control a display to show the received images; store permanently in one or more memory units in response to a user input one or more single images or one or more streams of images received from the image capturing device together with the received metadata, whereby a database is created in the one or more memory units storing for a plurality of previously performed endoscopic procedures one or more single images or stream of images together with the metadata, wherein the method further comprises the step of at least partly anonymizing the database by overwriting at least some of the metadata for each of the plurality of previously performed endoscopic procedures with new data.

13. A computer program product comprising program code means adapted to cause a processing unit to perform the steps of the method according to item 12, when said program code means are executed by the processing unit.

14. A computer program product according to item 13, wherein said computer program product comprises a non-transitory computer-readable medium having stored thereon the program code means.

15. A method of managing data stored in an image recording unit having a normal state and an error state of operation, the method comprising, by the image recording unit: receiving metadata; receiving images generated by an image sensor of a medical visualization device while a medical procedure is in progress, the images corresponding to optical images received by the image sensor; responsive, in the normal state, to a first user input, storing the images and the metadata in a memory, the images comprising single images or video; and in the error state, anonymizing at least some of the metadata.

16. A method according to item 15, further comprising: receiving a second user input; and responsive to receiving the second user input, switching the image recording unit from the normal state to the error state.

17. A method according to item 16, further comprising: receiving a message from another processing unit, the another processing unit being separate from the image recording unit, the message prompting a user to confirm switching of the image recording unit from the normal state to the error state; and controlling a display to show the message, wherein receiving the second user input comprises receiving the second user input from the another processing unit.

18. A method according to item 16, further comprising: before anonymizing the at least some of the metadata, creating a safety copy of the at least some of the metadata.

19. A method according to item 16, further comprising: before anonymizing the at least some of the metadata, creating an encrypted copy of the at least some of the metadata using an encryption key stored on the memory unit; and storing the encrypted copy in a memory unit remote from the image recording unit.

20. An image recording unit comprising logic operable to execute a method according to items 15-19.

21. A computer program product comprising program code configured to cause a processing unit to perform a method according to items 15-19.

22. An endoscopic system comprising an image recording unit comprising logic operable to execute a method according to items 15-19 and a medical visualization device comprising an image sensor.

Although some embodiments have been described and shown in detail, the invention is not restricted to them but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same hardware components. The mere fact that certain measures are recited in mutually different dependent items or described in different embodiments does not indicate that a combination of these measures cannot be used to advantage.

"About" as used herein when referring to a measurable value such as an amount, a temporal duration, and the like, is meant to encompass variations of ±20%, ±10%, ±5%, ±1%, and ±0.1% from the specified value, as such variations are appropriate. It is to be understood that in the present specification, the use of the term "about" in connection with a numerical value also affords support for the exact numerical value as though it had been recited without the term "about".

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

It should be emphasized that the term "comprises/comprising" are generally interpreted to be open ended terms which specify the presence of stated features, integers, steps or components but do not preclude the presence or addition of one or more other features, integers, steps, components or groups thereof. The terms "consisting of" or "consists of" are closed terms, and include only the components, structures, steps, or the like specifically listed in conjunction with such terms, as well as that which is in accordance with U.S. Patent law.

The invention claimed is:

1. An image recording unit comprising:
   a memory unit having embedded therein a database configured to store images and metadata, the images comprising single images and/or a stream of images, and the metadata specifying information about the patient and/or the endoscopic procedure associated with the images;
   a connection unit adapted to communicatively connect with an endoscope having an image sensor configured to generate the images, the images corresponding to optical images received by the image sensor; and a processing unit configured to receive the images from the image sensor via the connection unit, wherein the processing unit has a normal state of operation and an error state of operation, wherein, in the normal state, the processing unit is configured to:

receive the metadata;

receive the images captured by the image sensor of the endoscope;

control a display to show the images; and in response to a first user input, store the images and the metadata in the memory, and wherein, in the error state, the processing unit is configured to:

overwrite with new data at least some of the metadata.

2. An image recording unit according to claim 1, wherein, in the error state, the processing unit is configured to prevent images captured by the image sensor to be shown on the display.

3. An image recording unit according to claim 1, wherein the processing unit is configured to switch from the normal state to the error state in response to a second user input.

4. An image recording unit according to claim 3, wherein the image recording unit further comprises a user input unit operationally connected to the processing unit, and wherein the second user input can be generated using the user input unit.

5. An image recording unit according to claim 4, wherein the user input unit comprises a switch recessed below an aperture to prevent actuation of the switch with a finger of a user.

6. An image recording unit according to claim 3, wherein the image recording unit comprises a user input unit and a communication unit, the communication unit configured to receive a message and the second user input from another processing unit, the another processing unit being separate from the image recording unit, wherein the message prompts a user to confirm, via the user input unit, switching of the processing unit from the normal state to the error state.

7. An image recording unit according to claim 6, wherein the processing unit is configured to, in response to receiving the second user input from the another processing unit, control the display to show the message.

8. An image recording unit according to claim 3, wherein the processing unit is configured to, in the error state, prevent images captured by the image sensor to be shown on the display.

9. An image recording unit according to claim 1, wherein the processing unit is configured to, before overwriting the at least some of the metadata, create a safety copy of the at least some of the metadata.

10. An image recording unit according to claim 9, wherein the processing unit is configured to encrypt the safety copy using an encryption key.

11. An image recording unit according to claim 10, wherein the processing unit is configured to store the encrypted safety copy on a memory unit remote from the image recording unit, and wherein the encryption key is stored in the memory unit of the image recording unit.

12. An image recording unit according to claim 1, wherein the images are comprised in image files, each of the image files having an information zone, wherein the processing unit is configure to insert at least a part of the metadata into the information zone, and wherein the processing unit is configured to, when set to the error state, remove at least some of the metadata stored in the information zone.

13. An endoscopic system comprising an image recording unit according to claim 1 and an endoscope comprising an image sensor.

14. An endoscopic system according to claim 13, wherein the processing unit is configured to, before overwriting the at least some of the metadata, create a safety copy of the at least some of the metadata.

15. An endoscopic system according to claim 14, wherein the processing unit is configured to encrypt the safety copy using an encryption key.

16. An endoscopic system according to claim 15, wherein the processing unit is configured to store the encrypted safety copy on a memory unit remote from the image recording unit, and wherein the encryption key is stored in the memory unit of the image recording unit.

17. A method of managing data stored in an image recording unit, the method comprising:

by the image recording unit having a normal state and an error state of operation:

receiving metadata specifying information about a patient and/or an endoscopic procedure;

receiving images generated by an image sensor of an endoscope, the images corresponding to optical images received by the image sensor and comprising single images and/or a stream of images;

controlling a display to show the images;

in response to a first user input in the normal state, storing the images and the metadata in a memory of the image recording unit, and in the error state, overwriting with new data at least some of the metadata.

18. A method according to claim 17, further comprising:

receiving a second user input; and responsive to receiving the second user input, switching the image recording unit from the normal state to the error state.

19. A method according to claim 18, further comprising:

receiving a message from another processing unit, the another processing unit being separate from the image recording unit, the message prompting a user to confirm switching of the image recording unit from the normal state to the error state; and controlling the display to show the message, wherein receiving the second user input comprises receiving the second user input from the another processing unit.

20. A method according to claim 18, further comprising:

before overwriting the at least some of the metadata, creating a safety copy of the at least some of the metadata.

21. A method according to claim 18, further comprising:

before overwriting the at least some of the metadata, creating an encrypted copy of the at least some of the metadata using an encryption key stored on the memory unit; and storing the encrypted copy in a memory unit remote from the image recording unit.

22. A computer program product comprising a non-transitory computer-readable medium including, embedded therein, program code configured to cause a processing unit to perform the method of claim 18.

* * * * *